United States Patent [19]

Garwood et al.

[11] 3,972,958
[45] Aug. 3, 1976

[54] CONVERSION OF COAL TO HIGH OCTANE GASOLINE

[75] Inventors: William E. Garwood, Haddonfield; Solomon M. Jacob; James C. Kuo, both of Cherry Hill, all of N.J.; John J. Wise, Media, Pa.

[73] Assignee: Mobil Oil Corporation, New York, N.Y.

[22] Filed: Apr. 8, 1975

[21] Appl. No.: 566,153

[52] U.S. Cl. .......................... 260/683.49; 252/373; 252/455 Z; 260/449 R; 260/683.61; 260/683.62; 260/683.58
[51] Int. Cl.² ...................... C07C 3/54; C07C 27/06
[58] Field of Search ...... 260/449 R, 683.49, 683.61, 260/683.62, 683.58, 683.43; 252/373, 455 Z

[56] References Cited
UNITED STATES PATENTS

| | | | |
|---|---|---|---|
| 2,257,074 | 9/1941 | Goldsby | 260/683.62 |
| 2,286,814 | 6/1942 | Kemp | 260/683.61 |
| 3,013,990 | 12/1961 | Breck | 252/455 Z |
| 3,254,023 | 5/1966 | Miale | 260/449 R |
| 3,850,839 | 11/1974 | Seglin et al. | 252/373 |
| R22,786 | 9/1946 | Goldsby | 260/683.62 |

*Primary Examiner*—G. J. Crasanakis
*Attorney, Agent, or Firm*—Charles A. Huggett; Michael G. Gilman

[57] ABSTRACT

An integrated process for converting coal to high octane gasoline by gasifying the coal in such manner as to form a gas comprising carbon oxides, hydrogen and methane; contacting this gas in one or a series of steps with one or a series of catalysts, respectively comprising a special high silica to alumina ratio zeolite; converting the carbon oxides and hydrogen by such contact to a product comprising water, high octane aromatic gasoline and light hydrocarbon gases; alkylating the $C_3$ and $C_4$ olefins with the isobutane in the light gases to produce alkylate gasoline; admixing the aromatic and alkylate gasoline; and subjecting the $C_2^-$ portion of the product to steam reforming whereby additional synthesis gas to be admixed with the gas produced by coal gasification is formed.

4 Claims, 2 Drawing Figures

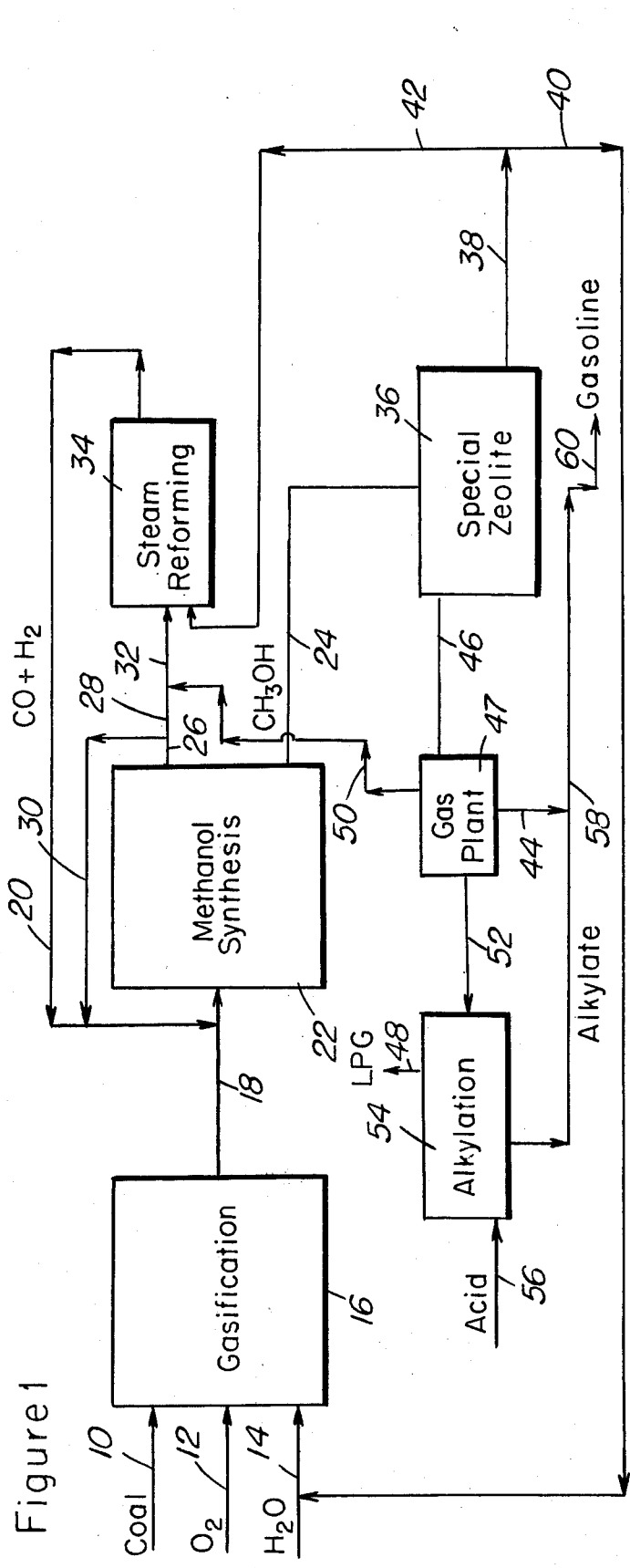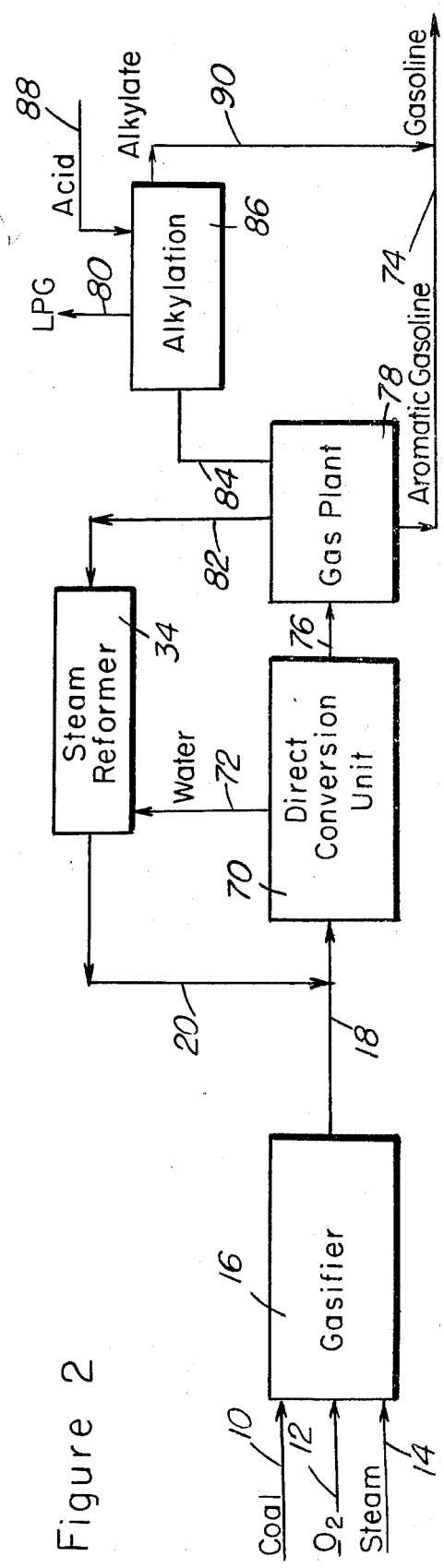

CONVERSION OF COAL TO HIGH OCTANE GASOLINE

This invention relates to the upgrading of coal. It more particularly refers to the efficient conversion of coal into high octane, liquid, hydrocarbon gasoline.

It is well known that many of the world's largest users of liquid petroleum products have less than adequate stocks and reserves of crude oil. These countries are therefore to a greater or lesser extent dependent upon crude oil obtained from foreign sources to help balance their energy needs. It is also true that many of these crude oil deficient countries and areas have large coal deposits. To date however, no really good process has been developed and commercialized for the conversion of coal to high quality automotive fuel including high octane gasoline.

It is known that coal can be gasified to a mixture of carbon oxides and hydrogen, as well as other components, which can be converted directly to aliphatic, lower octane gasoline by conventional Fischer-Tropsch catalysis. As is apparent, the quality of gasoline produced by such conventional Fischer-Tropsch catalysis leaves something to be desired in terms of octane number. It is unfortunate, but such Fischer-Tropsch gasoline is not economically readily upgraded by usual petroleum refinery technology, such as noble metal reforming.

There has recently been developed a new approach to the problem of converting coal or other solid fossil fuels to good quality liquid hydrocarbon gasoline. According to this new approach, advantage is taken of the unusual ability of a special group of crystalline alumino-silicate zeolites having a high silica to alumina ratio and offer constrained access to molecules to their pore structure to catalyze the conversion of methanol to high quality gasoline. Thus, coal is converted to synthesis gas comprising carbon monoxide and hydrogen which is converted to methanol which is in turn converted to high octane aromatic gasoline. In developing this process and other processes related to it, it has become apparent that while it is totally sound and practicable, certain significant improvements can be made in it, by some small modifications, depending upon the particular choice of specific upstream processes.

It is therefore an object of this invention to provide an improved process for converting coal to gasoline.

Other and additional objects will become apparent from a consideration of this entire specification including the claims and drawing hereof.

Understanding of this invention will be facilitated by reference to the accompanying drawing in which:

FIG. 1 is a schematic flow diagram of a particular processing embodiment of this invention; and FIG. 2 is a schematic flow diagram of a slightly different embodiment of this invention.

In accord with and fulfilling these objects, one aspect of this invention resides in a process comprising gasifying coal to a gas comprising carbon oxides, hydrogen and methane by a process which is capable of accomplishing this, such as the Lurgi process (see for example Scientific American, March 1974, Volume 230, No. 3, page 19 etc.). Such coal gasification processes are presently available commercial technology which are well documented and commercially practiced. No invention is here claimed in such coal gasification processes per se. After cleanup of this gas, or even without such cleanup, depending upon its sulfur content etc., it is converted to high quality aromatic gasoline by a process utilizing a catalyst comprising a special crystalline aluminosilicate to be described in detail below. Two alternatives are available for this conversion: one wherein the methane containing synthesis gas is contacted with a mixed catalyst comprising as a first component the special zeolite referred to above and detailed below and as a second component, a metal value having good carbon monoxide reduction catalytic activity and poor olefin hydrogenation activity, thus the second component comprises at least one metal, such as thorium, ruthenium, iron, cobalt or rhodium. This catalyst may also have an alkaline metal, such as potassium, associated therewith. The product is water and a full range of saturated and unsaturated hydrocarbons from $C_1$ to about $C_{10}$. The other alternative is to convert the carbon monoxide and hydrogen content of the methane containing synthesis gas to a product comprising methanol, using for example conventional methanol synthesis technology which is readily available from several commercial licensors, by employing a catalyst comprising zinc and copper. The organic portion of this methanol synthesis product, comprising methanol, is then contacted with a special zeolite catalyst and is thus converted to water and a full range of saturated and unsaturated hydrocarbons from $C_1$ to about $C_{10}$.

Regardless of which of these one step or polystep conversions are utilized, the product comprises water and a fully complement of hydrocarbons up to about $C_{10}$. The hydrocarbons are separated into $C_5^+$ gasoline, which is recovered as such, and a $C_4^-$ fraction which is resolved into an LPG fraction comprising predominantly saturated $C_3$ and $C_4$ components, an alkylation feed comprising isobutane and $C_3$ and $C_4$ olefins and a $C_2^-$ fraction comprising ethane, methane, hydrogen, carbon oxides and other low boilers. The alkylation feed is suitably alkylated in contact with an acid catalyst, conventionally a homogeneous acid catalyst such as sulfuric or hydrofluoric acid, in a conventional manner. Alkylation technology is generally available from various commercial sources and is widely practiced industrially. No invention is here claimed in this unit process per se. The alkylate product thereof is suitably admixed with the aforesaid aromatic gasoline to produce a remarkably high quality full range gasoline which can be used directly in motor vehicles, even high performance vehicles, without requiring octane appreciators, such as lead compounds.

According to this invention, the synthesis gas produced from coal contains methane. This material passes through the methanol synthesis process substantially unaltered. When the organic portion of the methanol synthesis product is converted to hydrocarbons as aforesaid, some additional methane and ethane are formed. Alternatively, in the one step direct conversion of synthesis gas to aromatic gasoline, the methane passes through the reaction substantially unchanged and there are made substantial quantities of methane and ethane.

In either case, the methane and ethane, from coal gasification or otherwise, together with hydrogen and carbon oxides if available, are converted by partial oxidation, steam reforming or the like with or without water gas shift so as to produce a properly proportioned auxiliary synthesis gas suitable for admixture with the synthesis gas produced by coal gasification and the mixture fed to direct or indirect (via methanol synthesis) aromatization. Part of the water necessary for this process can be supplied by the water produced in the aromatization unit process. As required, carbon dioxide can be periodically or continually purged from the system. Since coal is deficient in hydrogen relative to the carbon-hydrogen ratio desired in the product, either hydrogen must be added to the system or carbon must be removed from the system. It is preferred to do both in balance by adding water and rejecting carbon dioxide.

It is known that at least some present methanol synthesis catalysts are sulfur sensitive and that the special zeolite used in this invention is not sulfur sensitive. It is therefore within the scope of this invention to adjust the sulfur content of the synthesis gas produced by coal gasification if needed to accommodate catalysts used with this gas. This technology is per se known and may be employed or not as required.

It has been noted above that the coal gasification process to be used is the Lurgi process. This invention is dependent for its effectiveness upon the inclusion of some significant proportion of methane in the feed to the methanol synthesis unit process as aforesaid. At present the Lurgi coal gasification process seems to be best able to meet this requirement and thus has been specified. Other coal gasification processes which produce a product comprising proportions of about 1 to 5 molar parts of hydrogen to carbon monoxide and 0.1 to 1 molar parts of carbon dioxide to carbon monoxide would similarly be suitable. Since methane is substantially inert in the carbon monoxide reduction processes used herein, its proportional presence is not critical. It is not unusual for methane to be present in a proportion of about 0.2 to 1 mole per mole of carbon monoxide.

The special zeolite catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in type B catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000°F for at least 15 minutes. The zeolite is then flushed with helium and the temperature adjusted between 550°F and 950°F to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| TMA Offretite | 3.7 |
| ZSM-12 | 2 |
| Beta | 0.6 |
| ZSM-4(Omega) | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application, Ser. No. 358,192, filed May 7, 1973, the entire contents of which are incorporated herein by reference, describes a zeolite composition, and a method of making such, designated as ZSM-21 which is useful in this invention. Recent evidence has been adduced which suggests that this composition may be composed of at least two different zeolites, one or both of which are the effective material insofar as the catalysis of this invention is concerned. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000°F for one hour, for example, followed by base exchange with ammonium salts followed by calcination at 1000°F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 100°F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of ree space within the crystal, which might be expected to result in more stable structures. This free space, however, seems to be important as the locus of catalytic activity.

Crystal framework densities of some typical zeolites including some which are not within the preview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

According to this invention, coal, oxygen and steam are reacted together at a temperature of about 1450° to 1800°F to produce a synthesis gas product comprising methane, carbon oxides and hydrogen. This gas may also contain water. The synthesis gas may be subjected to a water gas shift reaction if desired so that the ratio of hydrogen to carbon monoxide is about 1 to 5 to 1. Ratios of carbon dioxide to carbon monoxide of about 0.1 to 1 to 1 are suitable.

The synthesis gas is converted to high octane aromatic gasoline by either a one step direct process or a two step process utilizing a methanol intermediate. In the direct process, the synthesis gas is converted over a combination catalyst having as a first component the special zeolite referred to above and as the second component, a metal value which has good carbon monoxide reducing catalytic activity and poor olefin hydrogenation activity. Exemplary metals are ruthenium, thorium, rhodium, iron and cobalt. This direct process is carried out at about 300° to 800°F and 50 to 1500 psig.

In the two step process, the synthesis gas is converted in a first stage to a product comprising methanol. The catalyst suitably comprises zinc-copper. The process operates at about 350° to 650°F and 700 to 2500 psig. Thermodynamic equilibria dictate operating at incomplete conversion with a synthesis gas recycle ratio of about 4 to 10. The organic portion of the product comprising methanol is converted to aromatic gasoline over a special zeolite catalyst, as defined above, at about 500° to 1200°F. and about 0.5 to 50 LHSV.

The products of either the direct or the two step synthesis conversion are resolved into $C_5^+$ aromatic gasoline, water, and $C_4^-$ hydrocarbon gas including the methane originally produced in the coal gasification. The $C_4^-$ fraction is itself resolved into an LPG fraction comprising saturated $C_3$ and $C_4$'s, a $C_2^-$ fraction which is subjected to steam reforming and a $C_3 \times C_4$ olefin plus isobutane fraction which is alkylated with a homogeneous acid, e.g., hydrofluoric or sulfuric, catalyst at up to about 450°F and up to about 500 psig.

Referring now to the drawing and particularly to FIG. 1 thereof coal 10, oxygen 12 and steam 14 are suitably reacted 16 to produce a synthesis gas 18 which is admixed with auxiliary synthesis gas 20, to be described below, and the mixture converted 22 to a product comprising methanol 24. The unreacted portion of the synthesis gas 26 may be separated into a stream 28 comprising methane and a stream 30 comprising carbon monoxide and hydrogen, or it may be further processed without resolution. In either case, a stream comprising methane 28 is steam reformed 34 to produce auxiliary synthesis gas 20. The organic portion of the product comprising methanol 24 is converted to gasoline using a special zeolite 36. The product from this conversion comprises water 38, which is recycled either to coal gasification 40 or to steam reforming 42 or both, and hydrocarbons 46 comprising $C_5^+$ aromatic gasoline 44, and $C_4^-$ hydrocarbon. The hydrocarbon fraction is resolved in a gas plant 47 to recover a $C_2^-$ tail gas 50, which is fed to the steam reformer 34, and an alkylation feed 52. Alkylation 54 using an acid catalyst 56 produces alkylate 58 which is blended with the previously produced aromatic gasoline 44 to yield the final full range, high quality gasoline product 60.

Referring now to FIG. 2, the same coal gasifier as in FIG. 1 is used but in this case the synthesis gas 18 is fed to a direct conversion unit 70 containing carbon monoxide reducing catalyst and special zeolite catalyst. The product of this direct conversion is separated into water 72, which may be recycled to the steam reformer 34, and hydrocarbons 76, comprising $C_5^+$ aromatic gasoline 74 and $C_4^-$ gas, which is resolved in a gas plant 78, a $C_2^-$ tail gas stream 82 which is fed to the steam reformer 34 and an alkylation feed 84 comprising $C_3$ and $C_4$ hydrocarbons. Alkylation 86 utilizes an acid catalyst 88 to produce $C_7$ and $C_8$ alkylate 90 which is admixed with the prior produced aromatic gasoline 74 to constitute full range, high octane gasoline product 92.

The various unit processes of this invention can be carried out in fixed, fluidized or transport type catalyst beds. Appropriate heat exchange can be provided as required.

The product gasoline is an excellent lead-free motor fuel. In fact, it has such high quality that it can be blended with substantial volumes of lower octane materials such as straight run naphtha to increase its volume while still maintaining excellent quality.

What is claimed is:

1. A process of converting coal to gasoline comprising:
   a. reacting coal with oxygen and water at about 1450° to 1800°F to produce a synthesis gas product comprising carbon oxides, hydrogen and methane;
   b. catalyzing the conversion of said synthesis gas product from step (a) to form a product comprising water, $C_4^-$ gas and $C_5^+$ liquid hydrocarbons with a catalyst comprising a crystalline aluminosilicate zeolite having a silica to alumina ratio of at least 12 and a constraint index of 1 to 12;
   c. separating a gasoline fraction containing aromatic components therein from said liquid hydrocarbons of step b;
   d. separating said $C_4^-$ gas into a $C_2^-$ tail gas comprising methane, ethane and ethylene, and an alkylation feed comprising saturated and unsaturated $C_3$ and $C_4$ hydrocarbons;
   e. alkylating said alkylation feed in contact with a strong alkylation acid to a reaction temperature up to about 450°F and up to about 500 psig;
   f. separating $C_7$ and $C_8$ alkylate from step (e) and admixing said alkylate with said gasoline from step (c);

g. steam reforming said $C_2^-$ tail gas from step (d) to form an auxiliary synthesis gas comprising carbon oxides and hydrogen; and h. admixing said auxiliary synthesis gas from step (g) with said coal gasification gas from step (a) prior to conversion thereof in step (b).

2. The process claimed in claim 1 including contacting said synthesis gas with a catalyst comprising said zeolite as a first component and as a second component a metal value having high catalytic acitivity for reducing carbon monoxide and low catalytic activity for hydrogenating olefins, at about 300° to 800°F and about 50 to 1500 psig; recovering a $C_2^-$ fraction and steam reforming such.

3. The process claimed in claim 2 wherein said metal value is at least one member selected from the group consisting of thorium, ruthenium, iron, rhodium and cobalt.

4. The process claimed in claim 1 wherein said zeolite is a ZSM-5.

* * * * *

UNITED STATES PATENT AND TRADEMARK OFFICE
CERTIFICATE OF CORRECTION

PATENT NO. : 3,972,958
DATED : August 3, 1976
INVENTOR(S) : WILLIAM E. GARWOOD, SOLOMON M. JACOB, JAMES C. KUO and JOHN J. WISE It is certified that error appears in the above-identified patent and that said Letters Patent are hereby corrected as shown below:

Column 5, line 20,      "zeolities" should be --zeolites--.

Column 6, line 11,      "100°F" should be --1000°F--.

Column 7, line 59,      "$C_3 \times C_4$" should be --$C_3 + C_4$--.

Signed and Sealed this

Thirtieth Day of November 1976

[SEAL]

*Attest:*

RUTH C. MASON
*Attesting Officer*

C. MARSHALL DANN
*Commissioner of Patents and Trademarks*